(12) United States Patent
Barneck et al.

(10) Patent No.: US 10,870,015 B2
(45) Date of Patent: Dec. 22, 2020

(54) METHODS AND APPARATUS TO DELIVER THERAPEUTIC NON-ULTRAVIOLET ELECTROMAGNETIC RADIATION FOR AN ENDOTRACHEAL TUBE

(71) Applicants: Mitchell D. Barneck, Portland, OR (US); Nathaniel L. Rhodes, Murray, UT (US); Martin de la Presa, Salt Lake City, UT (US); Arash E. Poursaid, Sandy, UT (US)

(72) Inventors: Mitchell D. Barneck, Portland, OR (US); Nathaniel L. Rhodes, Murray, UT (US); Martin de la Presa, Salt Lake City, UT (US); Arash E. Poursaid, Sandy, UT (US)

(73) Assignee: LIGHT LINE MEDICAL, INC., Salt Lake City, UT (US)

( * ) Notice: Subject to any disclaimer, the term of this patent is extended or adjusted under 35 U.S.C. 154(b) by 0 days.

(21) Appl. No.: 15/141,511

(22) Filed: Apr. 28, 2016

(65) Prior Publication Data
US 2016/0317832 A1 Nov. 3, 2016

Related U.S. Application Data

(60) Provisional application No. 62/154,789, filed on Apr. 30, 2015, provisional application No. 62/292,028, filed on Feb. 5, 2016.

(51) Int. Cl.
*A61N 5/06* (2006.01)
*A61M 16/04* (2006.01)
(Continued)

(52) U.S. Cl.
CPC .............. *A61N 5/0603* (2013.01); *A61L 2/08* (2013.01); *A61M 16/04* (2013.01);
(Continued)

(58) Field of Classification Search
CPC ............... A61N 5/0603; A61N 5/0624; A61N 2005/0604; A61N 2005/0651;
(Continued)

(56) References Cited

U.S. PATENT DOCUMENTS 5,913,816 A 6/1999 Sanders et al.
7,473,219 B1 * 1/2009 Glenn ................ A61B 1/00068
600/114

(Continued)

FOREIGN PATENT DOCUMENTS

| WO | WO2010/047672 | 4/2010 |
| WO | WO2013/049491 | 4/2013 |
| WO | WO 2014/004762 | 1/2014 |

*Primary Examiner* — Kendra D Carter
*Assistant Examiner* — Elliot S Ruddie
(74) *Attorney, Agent, or Firm* — Madison IP, P.C.

(57) ABSTRACT

A therapeutic endotracheal tube assembly is provided for insertion into a patient's trachea to ventilate, to maintain patency of the patient's airway, and to deliver therapeutic electromagnetic radiation (EMR) to the patient. The therapeutic endotracheal tube assembly has an endotracheal tube and an EMR delivery system. The EMR delivery system has an EMR source for emitting non-ultraviolet, therapeutic EMR having intensity sufficient to activate desired therapeutic properties within the patient and an EMR conduction line conducive to the propagation of EMR from the EMR source along the endotracheal tube. The EMR conduction line is removably insertable into the endotracheal tube. The therapeutic endotracheal tube assembly may be custom made or may be constructed by retrofitting a removably insertable EMR delivery system to an existing endotracheal tube.

16 Claims, 11 Drawing Sheets

(51) Int. Cl.
*A61M 16/08* (2006.01)
*A61L 2/08* (2006.01)
*A61N 5/067* (2006.01)

(52) U.S. Cl.
CPC .... *A61M 16/0434* (2013.01); *A61M 16/0486* (2014.02); *A61M 16/0816* (2013.01); *A61M 16/0833* (2014.02); *A61M 2205/051* (2013.01); *A61M 2209/10* (2013.01); *A61N 2005/063* (2013.01); *A61N 2005/0604* (2013.01); *A61N 2005/067* (2013.01); *A61N 2005/0651* (2013.01); *A61N 2005/0659* (2013.01); *A61N 2005/0663* (2013.01)

(58) Field of Classification Search
CPC .... A61N 2005/0659; A61N 2005/0663; A61N 2005/067; A61M 16/0461; A61M 16/0463; A61M 16/0465; A61M 16/0486; A61M 16/0434; A61M 16/0816; A61M 2205/051; A61M 2025/0019; A61M 25/0009; A61M 25/0017; A61M 25/0028; A61L 2202/24; A61L 2/084; A61L 2/085
USPC ............... 29/592.1; 128/207.14; 604/21
See application file for complete search history.

(56) References Cited

U.S. PATENT DOCUMENTS

| | | |
|---|---|---|
| 8,480,722 B2 | 7/2013 | Klepper |
| 8,556,950 B2 | 10/2013 | Rioux et al. |
| 8,574,490 B2 | 11/2013 | Haytman et al. |
| 8,779,386 B2 | 7/2014 | Bak |
| 2001/0001957 A1 | 5/2001 | Allgeyer et al. |
| 2002/0091424 A1* | 7/2002 | Biel ................ A61K 31/54 607/88 |
| 2006/0130846 A1 | 6/2006 | Rife |
| 2007/0219605 A1 | 9/2007 | Yaroslavsky et al. |
| 2008/0058649 A1* | 3/2008 | Boyden ............ A61B 5/0071 600/476 |
| 2008/0161748 A1 | 7/2008 | Tolkoff et al. |
| 2010/0261995 A1 | 10/2010 | McKenna et al. |
| 2012/0065698 A1 | 3/2012 | Errico et al. |
| 2012/0123208 A1* | 5/2012 | Remmerswaal ....... A61B 1/267 600/116 |
| 2013/0030249 A1* | 1/2013 | Vazales ............ A61B 1/0669 600/120 |
| 2013/0060188 A1* | 3/2013 | Bedwell ............ A61L 2/0047 604/21 |
| 2013/0267888 A1* | 10/2013 | Rhodes ............. A61N 5/0624 604/21 |
| 2013/0323119 A1 | 12/2013 | Alwan |
| 2014/0058253 A1* | 2/2014 | Prough ............ A61B 5/0095 600/424 |
| 2014/0150782 A1 | 6/2014 | Vazales et al. |
| 2014/0235942 A1* | 8/2014 | Hellstrom .......... A61N 5/0601 600/104 |
| 2015/0190649 A1* | 7/2015 | Gelfand ............ A61N 5/0601 607/92 |
| 2015/0343182 A1 | 12/2015 | Vazales et al. |
| 2016/0256646 A1 | 9/2016 | Vazales |

* cited by examiner

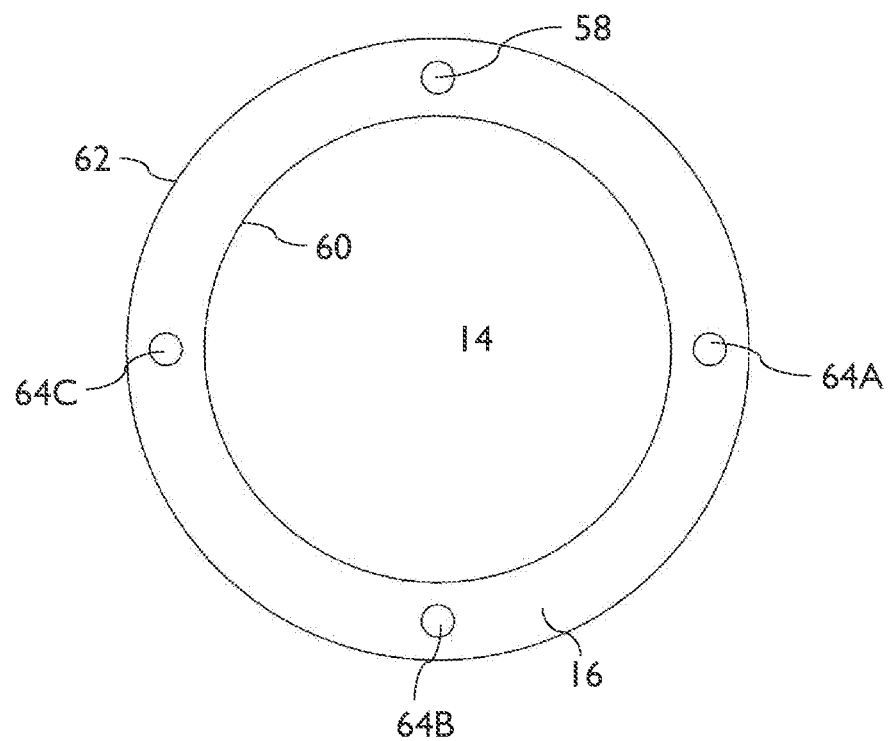
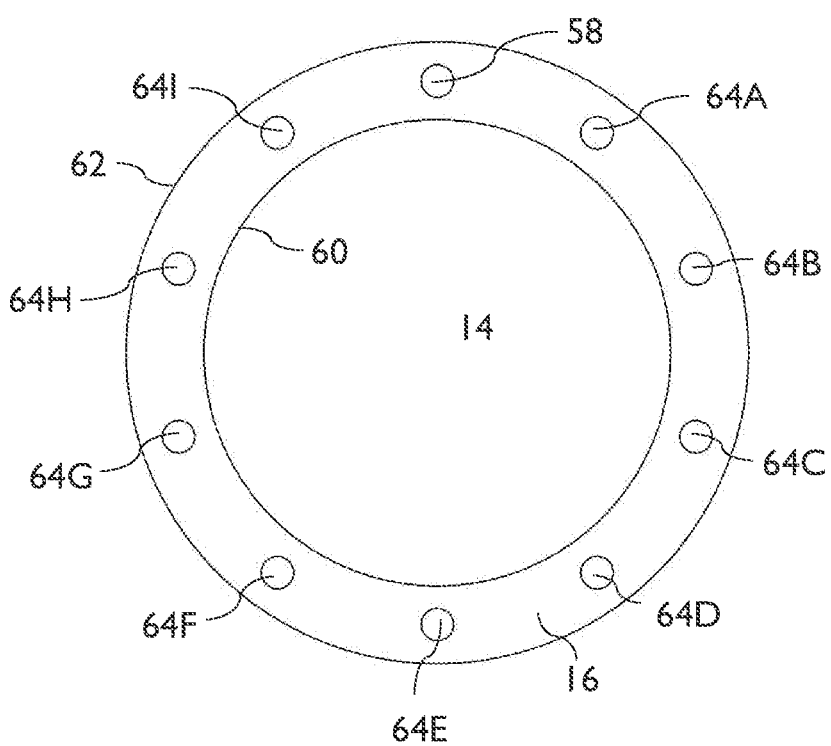

METHODS AND APPARATUS TO DELIVER THERAPEUTIC NON-ULTRAVIOLET ELECTROMAGNETIC RADIATION FOR AN ENDOTRACHEAL TUBE

RELATED APPLICATIONS

This application claims the benefit of U.S. Provisional Application No. 62/154,789 that was filed Apr. 30, 2015, for an invention titled METHODS AND APPARATUS TO INACTIVATE INFECTIOUS AGENTS ON AN ENDOTRACHEAL TUBE, which is hereby incorporated in its entirety by this reference. This application also claims the benefit of U.S. Provisional Application No. 62/292,028 that was filed Feb. 5, 2016, for an invention titled METHOD AND APPARATUS FOR REMOVABLE CATHETER VISUAL LIGHT STERILIZATION SYSTEM, which is hereby incorporated in its entirety by this reference.

This application is related to a co-pending application entitled METHODS AND APPARATUS TO INACTIVATE INFECTIOUS AGENTS ON A CATHETER RESIDING IN A BODY CAVITY, U.S. application Ser. No. 13/801,750, filed Mar. 13, 2013.

TECHNICAL FIELD

The present invention is a method and apparatus to provide therapeutic doses of non-ultraviolet light and/or sterilizing doses of non-ultraviolet light to stimulate healthy cell growth causing a healing effect and/or to inactivate infectious agents residing on, within, or generally around an endotracheal tube while said endotracheal tube is residing within a body cavity.

BACKGROUND

Endotracheal tubes are medical devices used to provide mechanical ventilation for incapacitated patients. Unfortunately, they commonly cause hospital-acquired pneumonia (HAP). These devices cause infections in 91,000-126,000 patients every year and are the leading cause of death among hospital-acquired infections (Scheld W M. Developments in the pathogenesis, diagnosis and treatment of nosocomial pneumonia. Surg Gynecol Obstet 1991; 172 Suppl: 42).

The current first-line standard of care treatment is antibiotics (American Thoracic Society, Infectious Diseases Society of America. Guidelines for the management of adults with hospital-acquired, ventilator-associated, and healthcare-associated pneumonia. Am J Respir Crit Care Med 2005; 171:388). However, establishing the diagnosis of ventilator-associated pneumonia (VAP) can be difficult due to concomitant etiologies and symptoms, leading to increased mortality. Additionally, the prevalence of drug-resistant bacteria often necessitates a more toxic second-line antibiotic treatment and, due to a greater side-effect profile, further increases the risk to patient safety.

Endotracheal tubes are known that function only to secure the airway and provide ventilation for the intubated patient. Various hydrophobic, antibiotic, and/or anti-inflammatory coatings for endotracheal tubes are also known. Examples of these coatings include antibiotic agents like chlorhexidine or silver. This coating is intended to inhibit bacterial and fungal colonization of the device. However, these proposals are only marginally effective in-vivo and are unable to prevent numerous infections and deaths.

There are also known methods for providing visualization at the tip of the endotracheal tube. While possibly helpful for the device insertion, this has not become a standard of care due to simpler methods being developed. This also does nothing to reduce the infection rates.

The use of ultraviolet (UV) light to reduce the prevalence of infection is known. Unfortunately, UV light is well known to cause damage to living cells (Riffle. "UV-light-induced signal cascades and skin aging." Ageing research reviews 1.4 (2002): 705-720).

Unfortunately, these methods and solutions fail to offer a reduction in hospital-acquired infections. This is due not only to the difficulty in diagnosing HAP in the midst of concomitant etiologies, but also to the high clinical prevalence of drug resistant microorganisms. Accordingly, there exists a need for a method and apparatus for delivering non-antibiotic, bactericidal therapeutics in-vivo, and for such a method and apparatus to use novel technology in delivering safe, effective, and reproducible disinfection.

SUMMARY OF THE INVENTION

The invention of the present disclosure comprises of a method and apparatus for delivering therapeutic doses in-vivo to stimulate healthy cell growth causing a healing effect and/or to inactivating infectious agents on or within an endotracheal tube. In particular, the exemplary embodiments of this disclosure allow for therapeutic treatments that stimulate healthy cell growth enhancing healing and/or that inactivate infectious agents while the endotracheal tube is residing within a patient's body cavity. Generally, this disclosure relates to an endotracheal tube assembly that incorporates the delivery of electromagnetic radiation (EMR) therapy in addition to the functions of existing standard of care endotracheal tubes (securing airway, providing a passage for mechanical ventilation, etc.). The endotracheal tube assembly includes an endotracheal tube with an associated EMR source that provides non-ultraviolet, therapeutic EMR of sufficient fluency to inactivate one or more infectious agents and/or to stimulate healthy cell growth causing a healing effect.

For the purposes of this disclosure the use of the term "therapeutic" should be understood to mean of or relating to the treatment of disease, including infectious agents, as well as serving or performed to maintain health, including enhancing healthy cell growth.

It should also be understood that the exemplary embodiments of this disclosure include retrofitting a EMR delivery system to an existing standard endotracheal tube where the EMR delivery system is permanently attached to the endotracheal tube or where the EMR delivery system is removably insertable into the endotracheal tube, as well as including the use of a custom-made endotracheal tube that incorporates the EMR delivery system into the structure of the endotracheal tube. For a rapid, retrofit connection of the EMR delivery system onto the endotracheal tube a quick-connect coupling may be used and/or the insertable portion of the EMR delivery system may move freely and axially relative to the endotracheal tube.

This disclosure also provides methods and apparatuses for effectively sterilizing the body surface for the area in, on, or around the endotracheal tube. This is done through use of EMR at sufficient intensities capable of inactivation of infectious agents. This source can be from a single or group of EMR sources including, but not limited to, a light emitting diode, a semiconductor laser, a diode laser, an incandescent and fluorescent light source. This EMR source provides non-ultraviolet, sterilizing EMR providing one or more wavelengths in the range of approximately 380 nm to approximately 900 nm. In order to provide sufficient inactivation of infectious species each EMR wavelength should be of a narrow spectrum and centered around one wavelength from the group, and has intensity sufficient to inactivate one or more infectious agents. This group includes several wavelengths centered about: 400 nm, 405 nm, 415 nm, 430 nm, 440 nm, 455 nm, 470 nm, 475 nm, 660 nm, and 808 nm.

Of particular interest to this endotracheal tube assembly is the use of light between 380 and 900 nm wavelengths. Additionally, the intensity and power of the light emitted is particularly suitable for the inactivation of infectious agents, thus a range of fluency covering 0.1 J/cm$^2$ to 1 kJ/cm$^2$ and a range of powers from 0.005 mW to 1 W, and power density range covering 1 mW/cm$^2$ and 1 W/cm$^2$ are of interest for these device assemblies and methods.

The EMR delivery system directs the EMR lengthwise along the wall of said flexible tube in the plane of the flexure thereof for emission of the EMR internal and/or external to the endotracheal tube body. In most cases, EMR delivery system may be inserted such that its forward end terminates toward the forward end of the flexible, endotracheal tube body.

For each exemplary embodiment, the endotracheal tube assembly and method for disinfection could be utilized in an adjustable or predetermined duty cycle. If treatments began immediately after sterile procedure was initiated, device related infections may be inhibited. This includes device related biofilm growth.

BRIEF DESCRIPTION OF THE DRAWINGS

These and other features and advantages of the present disclosure will become more readily appreciated by referring to the following detailed description of exemplary embodiments when considered in connection with the accompanying drawings, which are not necessarily drawn to scale. It will be understood that said drawings depict exemplary embodiments and, therefore, are not to be considered as limiting the scope with regard to other embodiments which the invention is capable, wherein:

FIG. 9 is a cross sectional view of an exemplary custom-made endotracheal tube showing an embedded cuff inflating conduit and embedded optical conduits;

FIG. 10 is a cross sectional view of yet another exemplary custom-made endotracheal tube showing an embedded cuff inflating conduit and embedded optical conduits;

REFERENCE NUMERALS

Figure 1:
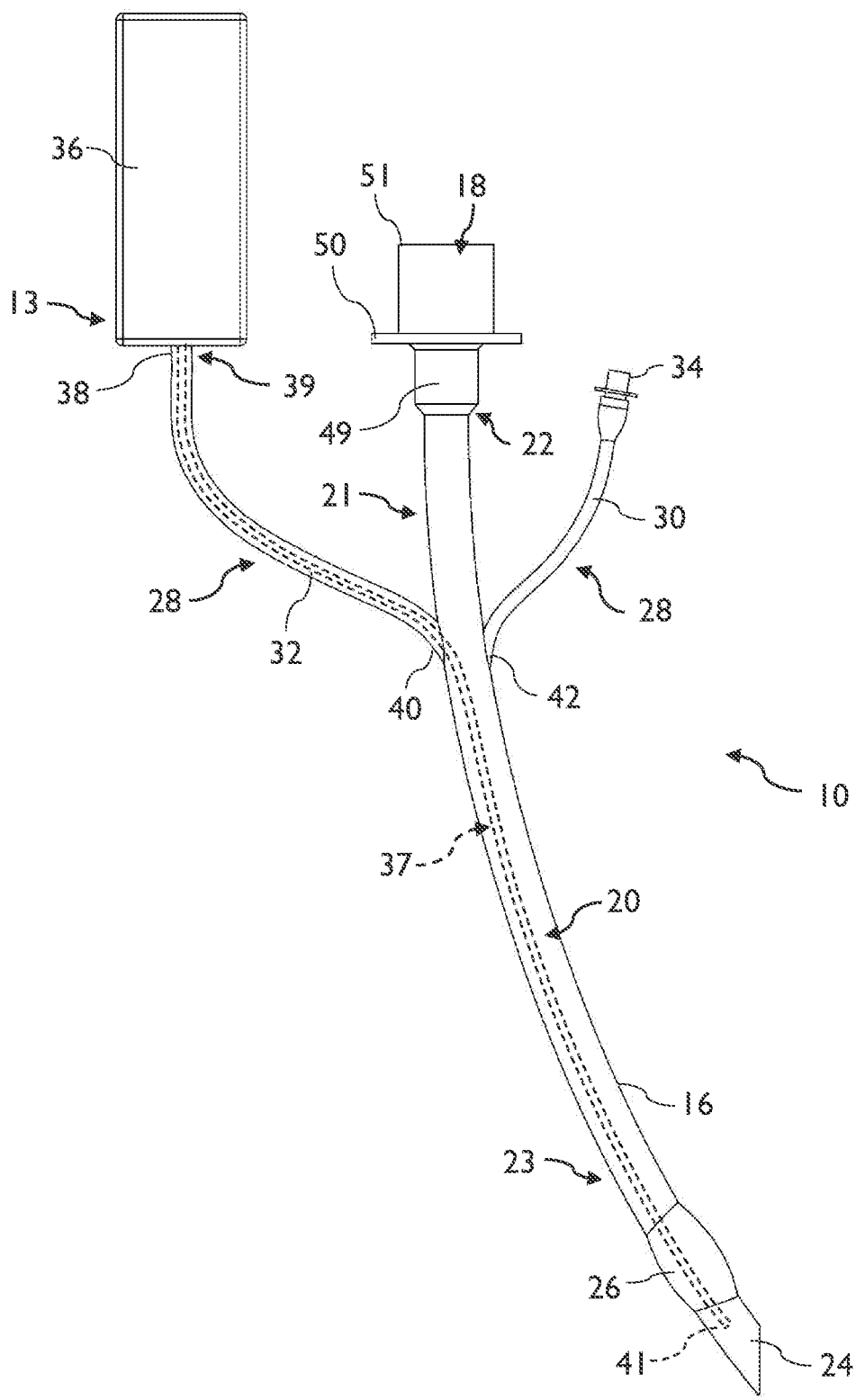
FIG. 1 is a profile view, illustrating an exemplary embodiment of a custom-made endotracheal tube with side ports for an inflation cuff and for an exemplary EMR delivery system.

| | |
|---|---|
| endotracheal tube assembly 10 | endotracheal tube 12 |
| EMR delivery system 13 | lumen 14 |
| tube wall 16 | ventilator collar 18 |
| tube body 20 | upper tube portion 21 |
| proximate end 22 | lower tube portion 23 |
| forward end 24 | inflatable cuff 26 |
| side ports 28 | cuff inflation conduit 30 |
| optical conduit 32 | cuff inflation fitting 34 |
| EMR source 36 | EMR conduction line 37 |
| EMR coupling 38 | coupling end 39 |
| optical joinder site 40 | distal end 41 |
| inflation joinder site 42 | combined joinder site 44 |
| combining site 46 | combined conduit 48 |
| connection sleeve 49 | stop flange 50 |
| engagement cylinder 51 | EMR directing ring 52 |
| cylindrical aperture 54 | centerline 56 |
| inflation cuff conduit 58 | internal surface 60 |
| external surface 62 | distal optical conduit(s) 64 (A-I) |
| optical conduit channel 66 | endotracheal adapter 68 |
| adapter body 69 | EMR port 70 |
| ventilator fitting end 71 | engagement end 72 |
| adapter stop flange 74 | ventilation channel 75 |
| EMR illumination 76 | secondary port 78 |
| first inner diameter 80 | first outer diameter 82 |
| second inner diameter 84 | second outer diameter 86 |

DETAILED DESCRIPTION

Various exemplary embodiments of the present disclosure are described more fully hereafter with reference to the accompanying drawings. These drawings illustrate some, but not all of the embodiments of the present disclosure. It will be readily understood that the components of the exemplary embodiments, as generally described and illustrated in the Figures herein, could be arranged and designed in a wide variety of different configurations. Thus, the following more detailed description of the exemplary embodiments of the apparatus, system, and method of the present disclosure, as represented in FIGS. 1 through 15, is not intended to limit the scope of the invention, as claimed, but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be coupled to each other even though they are not in direct contact with each other. The term "abutting" refers to items that are in direct physical contact with each other, although the items may not necessarily be attached together.

The word "exemplary" is used exclusively herein to mean "serving as an example, instance, or illustration." Any embodiment described herein as "exemplary" is not necessarily to be construed as preferred or advantageous over other embodiments.

While the various aspects of the embodiments are presented in drawings, the drawings are not necessarily drawn to scale unless specifically indicated.

Referring now to FIG. 1 of the present disclosure, an endotracheal tube assembly 10 is shown in a profile view. The endotracheal tube assembly 10 is capable of insertion into a patient's trachea to ventilate, to maintain patency of the patient's airway, and to deliver therapeutic electromagnetic radiation (EMR) to the patient.

Figure 2:
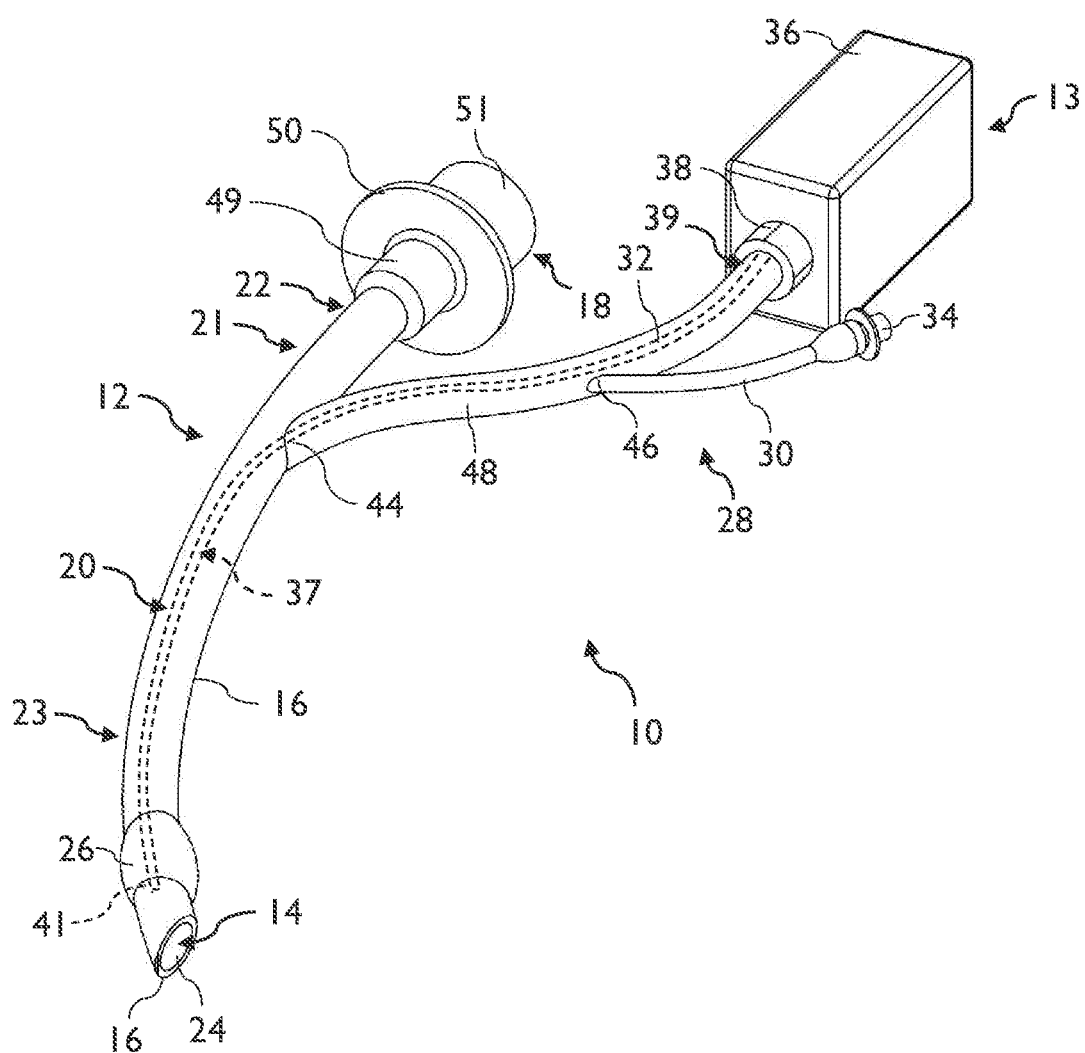
FIG. 2 is a perspective view illustrating another exemplary embodiment of a custom-made endotracheal tube with a branched side port for accommodating an inflation cuff and for an exemplary EMR delivery system.

FIGS. 1 and 2 illustrate that the therapeutic endotracheal tube assembly 10 comprises an endotracheal tube 12 and an EMR delivery system 13 having a lumen 14 defined by a tube wall 16 and a ventilator collar 18. The endotracheal tube 12 has tube body 20 with an upper tube portion 21 having a proximate end 22 and a lower tube portion 23 having a forward end 24 for insertion into the patient's trachea. The proximate end 22 of the upper tube portion 21 of the tube body 20 is coupled to the ventilator collar 18 in any suitable manner. Further, the endotracheal tube 12 typically has an inflatable cuff 26 surrounding the tube wall 16 proximate the forward end 24. The lumen 14 of the endotracheal tube 12 is used principally to pass ventilating gas from the ventilator (not shown) to the patient's lungs. However, the lumen 14 may be used as conduit for the passage of medical instruments of various kinds, including the EMR delivery system 13 of this disclosure. Also, it should be understood that a secondary lumen (not shown in FIGS. 1 and 2, but see FIG. 13 for examples of secondary lumens) may be used as a conduit for the insertable portions of the EMR delivery system 13.

In the exemplary embodiment of FIG. 1, the endotracheal tube 12 has two separate side ports 28, a cuff inflation conduit 30 and an optical conduit 32. The cuff inflation conduit 30 has a cuff inflation fitting 34 through which an inflation fluid is injected to inflate the inflatable cuff 26 to seal the trachea or removed to deflate the inflatable cuff 26 so that the endotracheal tube 12 may be removed from the patient's trachea. The optical conduit 32 receives the EMR delivery system 13 as will be described more fully below.

The exemplary embodiment of FIG. 2 differs from the embodiment in FIG. 1 in that the endotracheal tube 12 has a single, combined side port 28 because the cuff inflation conduit 30 ports into the optical conduit 32. Although there are endotracheal tubes 12 that have two side ports 28, to best accommodate the EMR delivery system 13, the exemplary embodiments of FIGS. 1 and 2 would most likely be custom made for optimum compatibility with the EMR delivery system 13. Nevertheless, if one of the side ports 28 in an off-the-self, multiple side port endotracheal tube 12 is suitably compatible with the EMR delivery system 13, then such an endotracheal tube 12 need not be custom made.

The EMR delivery system 13 comprises an EMR source 36 for emitting non-ultraviolet, therapeutic EMR having intensity sufficient to activate desired therapeutic properties within the patient, an EMR conduction line 37 (shown in phantom lines) conducive to the propagation of EMR from the EMR source 36 along the endotracheal tube 12, and an EMR coupling 38 to connect the EMR source 36 to a coupling end 39 of the EMR conduction line 37. Such desired therapeutic properties within the patient may include stimulating healthy cell growth or sterilizing one or more target organisms or infectious agents.

The EMR source 36 may comprise an optical element (not shown) such as light emitting diodes, lasers, filtered fluorescents, filtered incandescents, and any combination thereof. The EMR source 36 may provide non-ultraviolet, sterilizing EMR at one or more wavelengths in the range of approximately 380 nm to approximately 900 nm. In order to provide sufficient inactivation of infectious agents, each EMR wavelength should be of a narrow spectrum centered about a wavelength that has demonstrated sterilization when applied at an intensity sufficient to inactivate one or more infectious agents. Several exemplary wavelengths have demonstrated desirable sterilization, including those wavelengths centered about: 400 nm, 405 nm, 415 nm, 430 nm, 440 nm, 455 nm, 470 nm, 475 nm, 660 nm, and 808 nm.

Of particular interest to this endotracheal tube assembly 10 is the use of light between 380 and 900 nm wavelengths. Additionally, the intensity and power of the light emitted is particularly suitable for the inactivation of infectious agents, thus a range of fluency covering 0.1 $J/cm^2$ to 1 $kJ/cm^2$ and a range of powers from 0.005 mW to 1 W, and power density range covering 1 $mW/cm^2$ and 1 $W/cm^2$ are of interest for these device assemblies and methods.

Also of interest to this endotracheal tube assembly 10 is the use of use of different wavelengths between 532 and 1064 nm for stimulating tissue healing properties. Exemplary wavelengths have demonstrated desirable tissue healing properties, including those wavelengths centered about 633 nm, 808 nm, and 830 nm. Doses ranging from 0.09 to 90 $J/cm^2$ have been demonstrated to be effective, with the predominating values from 1 to 5 $J/cm^2$. However, doses 150 $J/cm^2$ are of particular interest for the applications contemplated by this disclosure.

For each exemplary embodiment described herein, the endotracheal tube assembly 10 and method for disinfection could be utilized in an adjustable or predetermined duty cycle. If treatments began immediately after sterile procedure was initiated, device related infections may be inhibited. This includes device related biofilm growth.

A treatment may include at least one wavelength of therapeutic EMR that acts as a predominant wavelength selected to sterilize one or more target organisms and selected from the group of wavelengths centered about 400 nm, 405 nm, 415 nm, 430 nm, 440 nm, 455 nm, 470 nm, 475 nm, 660 nm, and 808 nm. Another treatment may include alternating the predominant wavelength between a first predominant wavelength and a second predominant wavelength (differing from the first predominant wavelength) in a selected treatment pattern. Further, sterilizing EMR and EMR that stimulates healthy cell growth may be transmitted simultaneously in tandem or alternatively.

The EMR conduction line 37 has the coupling end 39 and a distal end 41 and may be insertable into the endotracheal tube 12 to deliver non-ultraviolet, therapeutic EMR within the patient at sufficient intensity to activate desired therapeutic properties. The EMR conduction line 37 may comprise one or more optical features such as a reflective surface, an optically transmissible material, a lens, a fiber optic filament, a gradient modification, light emitting portions, opaque portions, or any combination thereof. The EMR conduction line 37 may also comprise plastic, silica, or other polymeric optical fiber capable of transmission and dispersion of light over a given distance.

Also, at least a portion of the endotracheal tube 12 may be optically clear or translucent. These portions of clearness or translucency permit the EMR emitted from the EMR conduction line 37 to deliver therapeutic EMR to the inside of the tube wall 16 and to body tissue external to the tube wall 16 and proximate the clear or translucent portions. In most cases, the endotracheal tube 12 will be an off-the-shelf (rather than custom made) item and the entire length of the endotracheal tube 12 will be clear or translucent. However, it should be understood that custom made endotracheal tubes 12 may have portions that are not clear or translucent so not to permit the emission of the EMR from the endotracheal tubes 12 at those opaque portions.

The EMR conduction line 37 may comprise at least one optical feature selected from a group of optical features such as a reflective surface, an optically transmissible material, a lens, a fiber optic filament, and any combination thereof. It also may be capable of transmitting more than one wavelength or intensity EMR. Multiple wavelengths may be transmitted simultaneously, one after another or in tandem, or a combination thereof (for example, one constantly on and the other wavelength pulsed). Multiple intensities may be transmitted through the same element simultaneously. Alternating patterns of light treatments may also be transmitted.

The optical conduit 32 may be incorporated onto, into, or through the endotracheal tube body 12 at optical joinder site 40 and the cuff inflation conduit 30 may be incorporated onto, into, or through the endotracheal tube body 20 at inflation joinder site 42, as shown in FIG. 1. The single, combined side port 28 of FIG. 2 may be incorporated onto, into, or through the endotracheal tube body 12 at combined joinder site 44 and the cuff inflation conduit 30 may be incorporated onto, into, or through the optical conduit 32 at a combining site 46. Together, the cuff inflation conduit 30 and the optical conduit 32 form a combined conduit 48.

The ventilator collar 18 depicted in FIGS. 1-5 represents a typical ventilator collar 18 known in the art. Of course, other types of connectors may be used to connect to a ventilator (not shown), and the ventilator collar 18 could be modified to accommodate a suitable connection of the endotracheal tube 12 to a ventilator without departing from the spirit of the invention. As depicted, the ventilator collar 18 comprises a connection sleeve 49 that secures the endotracheal tube 12 to the ventilator collar 18, a stop flange 50 to arrest over-engagement, and an engagement cylinder 51. Depending on the diameter of the ventilator connector (not shown), the ventilator may be coupled to the engagement cylinder 51 in either a snug male or female engagement.

Figure 3:
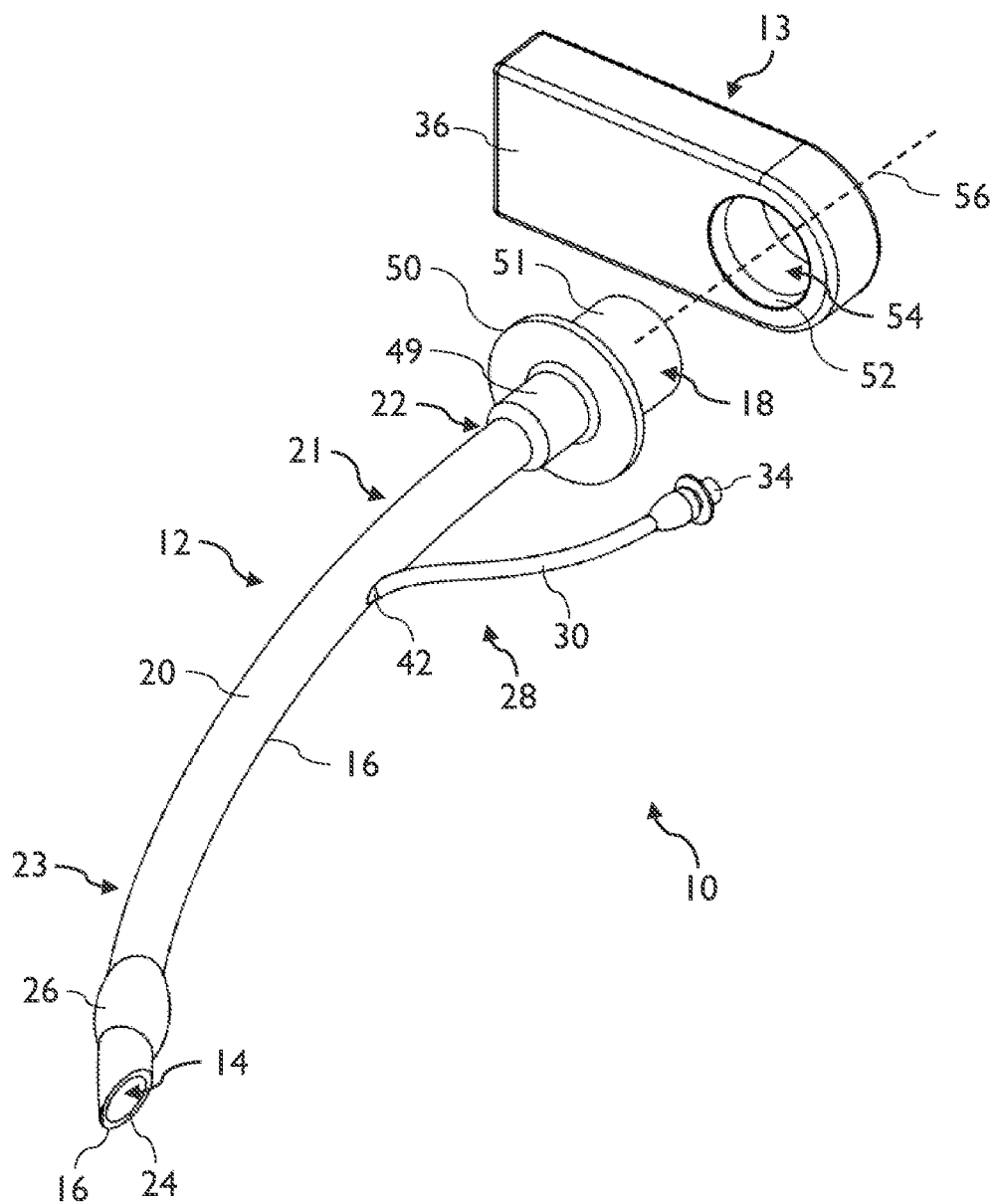
FIG. 3 is a perspective, exploded view illustrating yet another exemplary embodiment of a custom-made endotracheal tube with a side port for an inflation cuff and showing an EMR source that fits over the ventilator collar of the endotracheal tube.

FIG. 3 illustrates another exemplary embodiment that differs from the two previously described. With this embodiment, the endotracheal tube 12 has one or more embedded, partially embedded, or internally channeled EMR conduction lines 37 (not visible in FIG. 3, but described in more detail regarding FIGS. 9-13 below) and a single side port 28 for the cuff inflating conduit 30. The EMR source 36 has an EMR directing ring 52 disposed within a cylindrical aperture 54. The ventilator collar 18 and the cylindrical aperture 54 share a centerline 56 when the cylindrical aperture aligns for engagement with the engagement cylinder 51 of the ventilator collar 18. When the engagement cylinder 51 engages the cylindrical aperture 54 in male/female engagement, the EMR directing ring 52 communicates with the one or more embedded, partially embedded, or internally channeled EMR conduction lines 37 enable the propagation of EMR down the endotracheal tube 12. The communication of EMR from the EMR directing ring 52 to the EMR conducting lines 37 may be accomplished in any of a number of ways known to those skilled in the art, such as by direct contact of exposed ends of the EMR conducting lines 37 to the EMR directing ring 52 or through one or more collimating lenses or reflective mirrors (not shown). This configuration allows the EMR source 36 to be effectively coupled to all or part of the engagement cylinder 51 so that therapeutic EMR may be delivered into a patient's body without interfering with the coupling to the ventilator.

Figure 4:
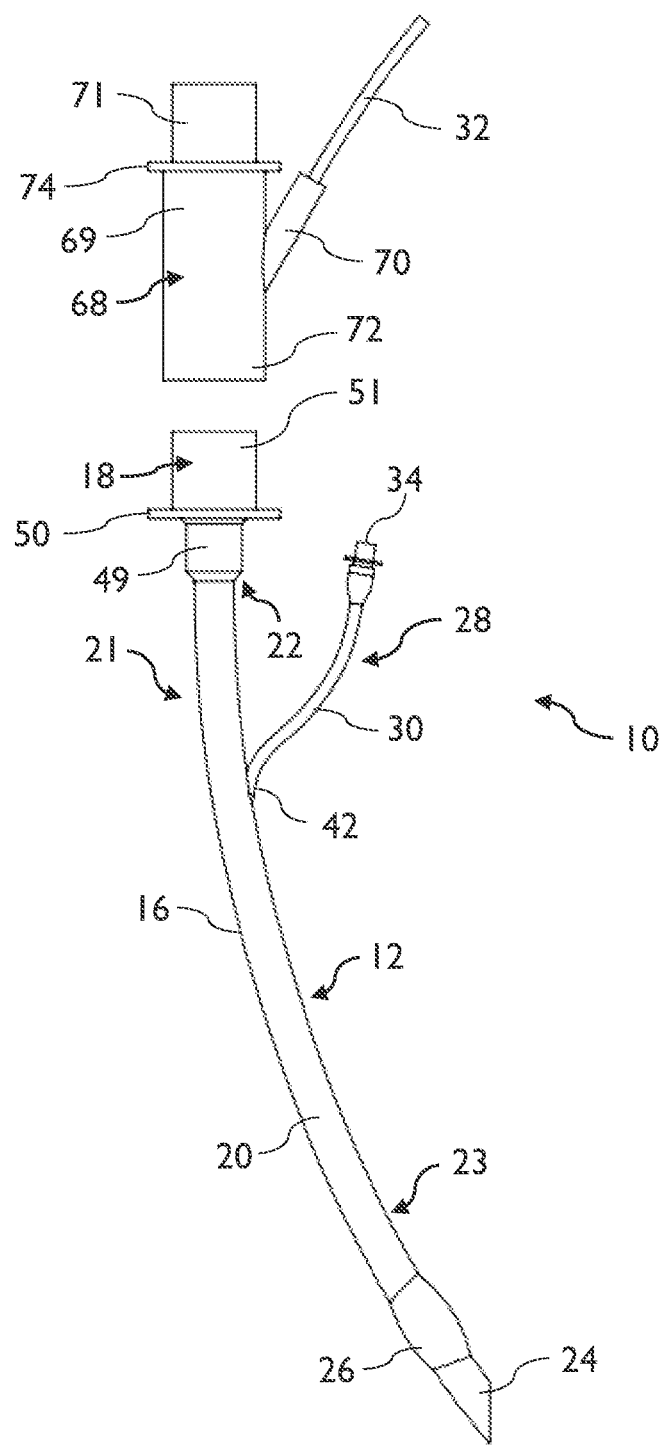
FIG. 4 is a profile, exploded view illustrating still another exemplary embodiment of an existing endotracheal tube that is retrofit with a port adapter to accommodate the insertion of an EMR conduction line of an EMR delivery system.
Figure 5:
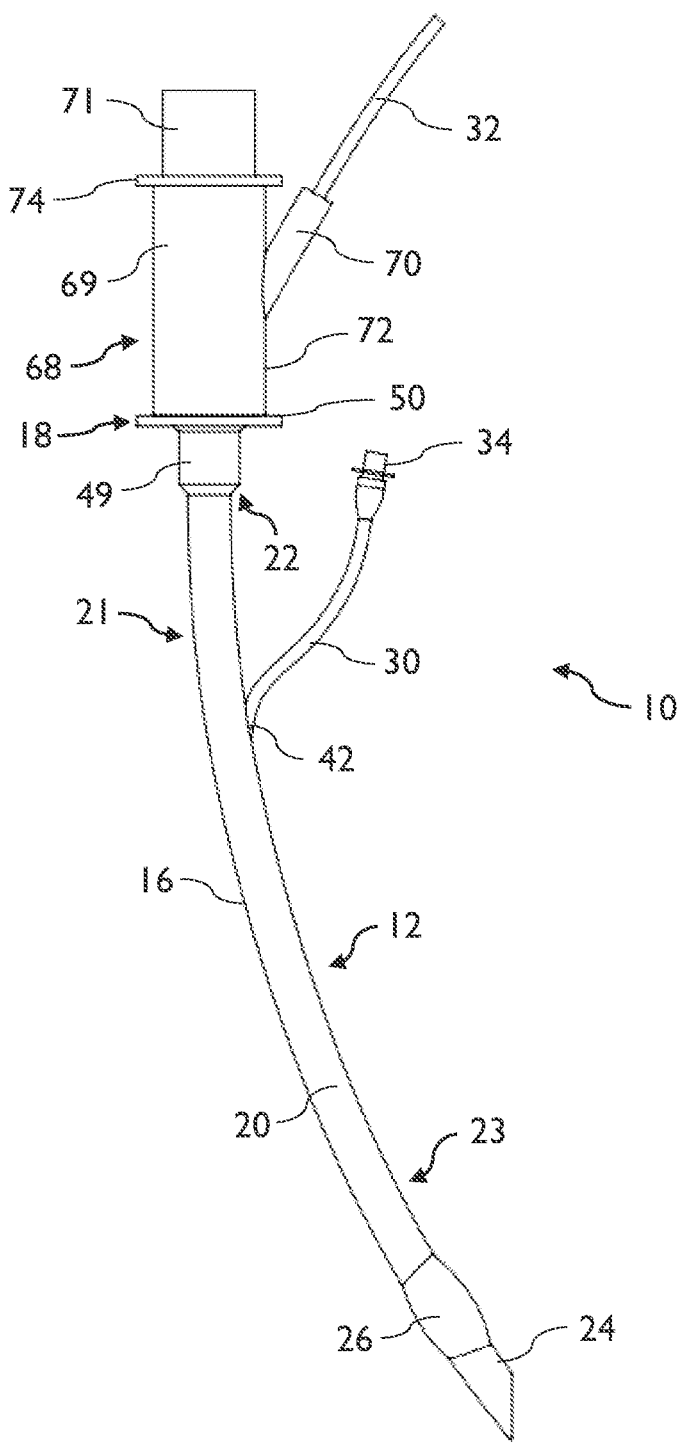
FIG. 5 is a profile view illustrating the exemplary embodiment of FIG. 4 showing the port adapter connected to the ventilation collar of the endotracheal tube.
Figure 15:
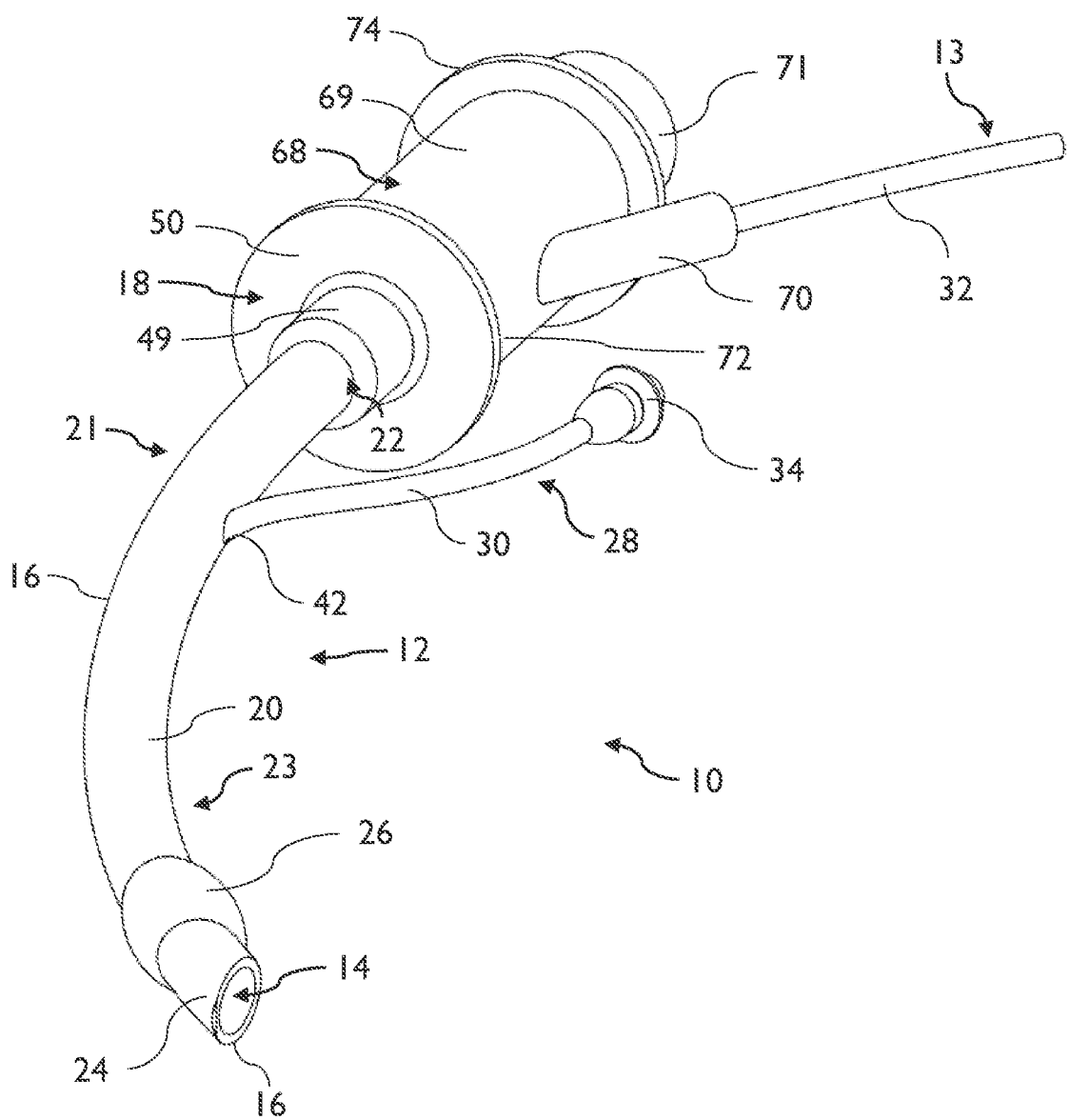
FIG. 15 is a perspective view of the exemplary embodiment of an existing endotracheal tube that is retrofit with a port adapter to accommodate the insertion of an EMR conduction line of an EMR delivery system.

FIGS. 4 and 5 depict first an exploded view of an exemplary embodiment of a therapeutic endotracheal tube assembly 10 (FIG. 4) and then an engaged view (FIG. 5). FIG. 15 is a perspective view of the therapeutic endotracheal tube assembly 10 in an engaged configuration. With this exemplary embodiment, an existing, off-the-shelf endotracheal tube 12 may be retrofitted with an endotracheal adapter 68 that converts the existing endotracheal tube 12 into a therapeutic endotracheal tube assembly 10 fully capable of delivering therapeutic EMR into a patient's body without interfering with the coupling to the ventilator. The endotracheal adapter 68 is disposed intermediate of the ventilator collar 18 and the ventilator.

The endotracheal adapter 68 of FIGS. 4-7 has an adapter body 69, an EMR port 70, a ventilator fitting end 71 corresponding in configuration to the engagement cylinder 51 of the ventilator collar 18, an engagement end 72 configured to engage the engagement cylinder 51 in male/female engagement, an adapter stop flange 74 for arresting over-engagement with the ventilator, and a ventilation channel 75 through which ventilation gas may travel without meaningful interference. The ventilation channel 75 of the port adapter 68 may accommodate passage of one or more of a diagnostic probe, a therapeutic tool, an additional energy source, an optical device, a surgical instrument, and a monitor into the endotracheal tube 12.

The EMR port 70 may have either an optical conduit 32 (as shown) or may receive the EMR conduction line 37 directly so long as the port is adequately sealed so that the ventilation operation will not be compromised. The form of seal may be any suitable seal known by those in the art, such as a rubber diaphragm that may be penetrated by the EMR conduction line 37 or O-rings positioned within the EMR port 70, or the like.

Figure 8:
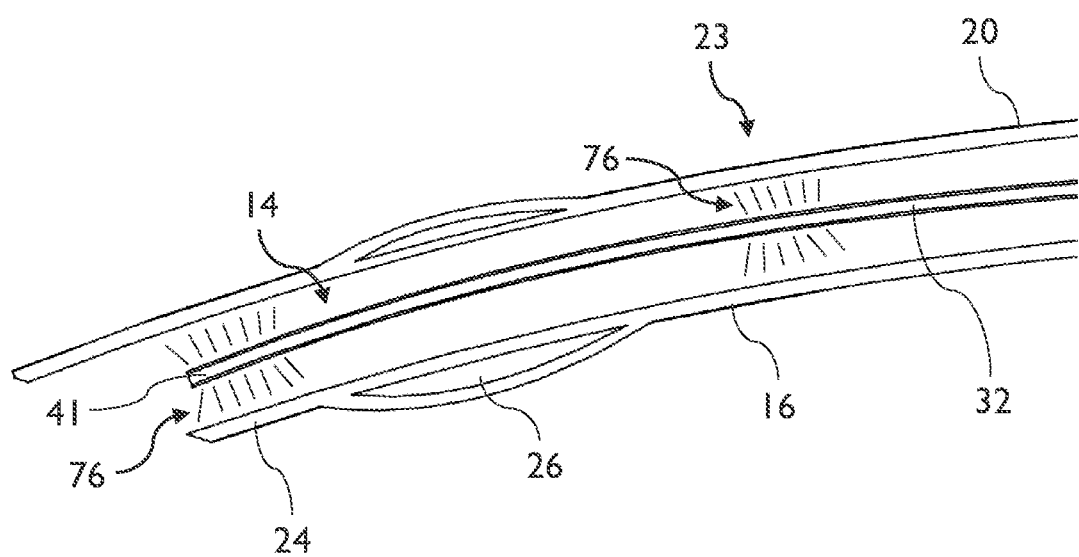
FIG. 8 is a cross sectional view of a lower portion of an exemplary endotracheal tube showing the insertion of an EMR conduction line within the lumen of the endotracheal tube.

The endotracheal adapter 68, as retrofitted, enables the removable insertion of the EMR conduction line 37 to whatever depth within or through the tube body 20 is desired. The EMR conduction line 37 is shown in FIG. 8 as being fully inserted within the tube body 20 where EMR illumination 76 is shown, by way of example, at the distal end 41 of the EMR conduction line 37. Of course, it should be understood that therapeutic EMR may be delivered anywhere along the length of the tube body 20 provided the tube body 20 is clear or translucent at least at those portions of the tube body 20 where emitted therapeutic EMR is desired and the EMR conduction line 37 emits EMR of sufficient intensity directed (radially, obliquely, longitudinally, from the distal end, and any combination thereof)

through the tube body 20 to the desired location(s). The methods and apparatus for providing gradient modification and/or multiple emission portions for the EMR conduction line 37 are described in co-pending application entitled METHODS AND APPARATUS TO INACTIVATE INFECTIOUS AGENTS ON A CATHETER RESIDING IN A BODY CAVITY, U.S. application Ser. No. 13/801,750, filed Mar. 13, 2013, which has been incorporated in its entirety by this and a previous reference.

Figure 6:
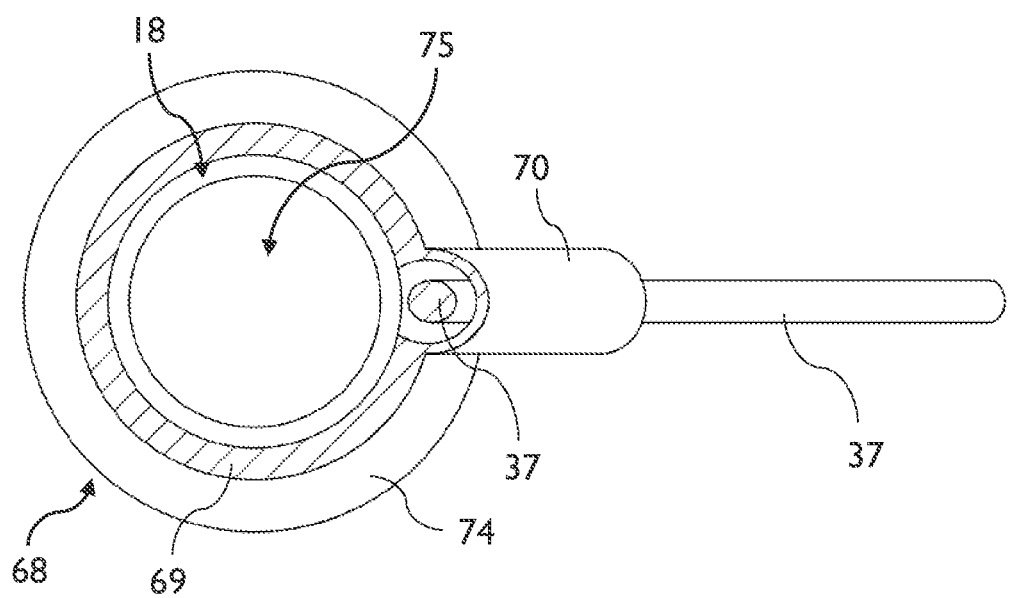
FIG. 6 is a cross sectional view of the exemplary port adapter illustrating the ingress point for the EMR conduction line into a through channel within the port adapter.
Figure 7:
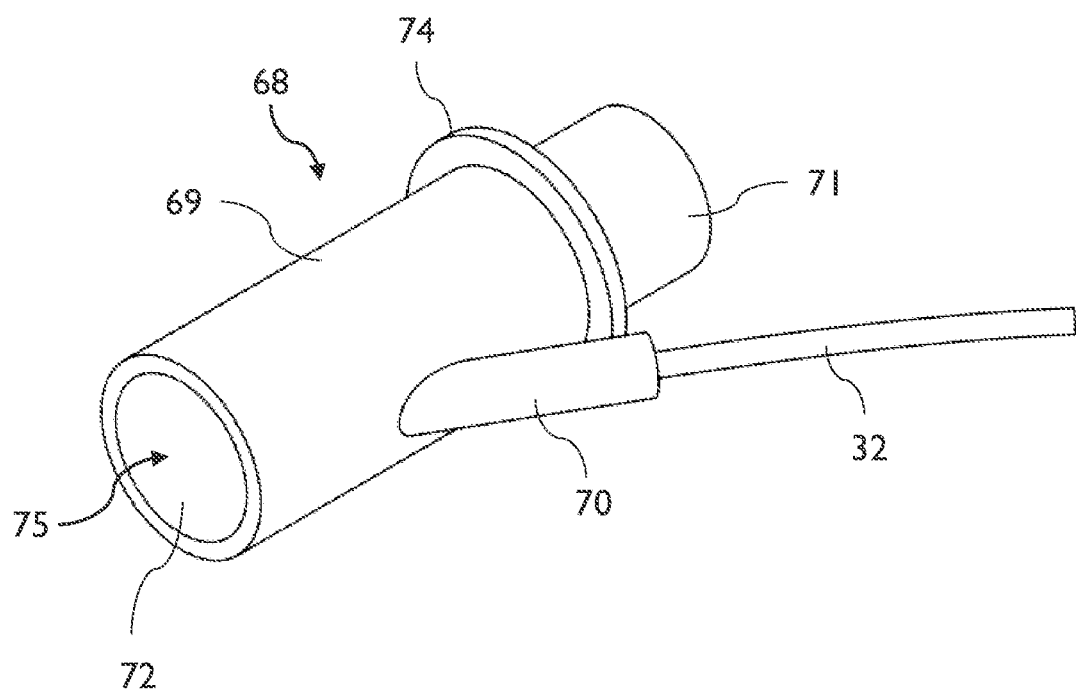
FIG. 7 is a perspective view of the exemplary port adapter of FIGS. 4-6.

By way of example, FIG. 6 shows the EMR conduction line 37 disposed directly within the EMR port 70 so that the EMR conduction line 37 may be inserted unobstructed into the ventilation channel 75 and then into the lumen 14 of the tube body 20 of the endotracheal tube 12 and may be subsequently removed.

Referring now to FIGS. 9-13 of the present disclosure, depicted are cross-sectional views of various exemplary configurations of the endotracheal tube body 20. The section taken is transverse to a longitudinal axis of the endotracheal tube body 20 at any point (other than at the balloon cuff 26) along the axis downstream of the most downstream joinder site 40, 42, 44. The cross-sectional views show a portion of the exemplary endotracheal tube bodies 20 sometimes identified herein as a distal endotracheal tube having a tube wall 16, bounded by an internal surface 60 and an external surface 62, encompassing the lumen 14, previously identified.

FIG. 9 illustrates one such configuration, wherein one or more distal optical conduits 64A-C are embedded in the endotracheal tube wall 16 between the internal surface 60 and the external surface 62. This configuration occurs distal to the site where the external optical conduit 32 ports into the endotracheal tube body 20. An embedded cuff inflation conduit 58 is the downstream extension of the cuff inflation conduit 30 and is located along the wall 16 of the endotracheal tube body 20 between the inflation joinder site 42 and the inflatable cuff 26.

Referring now to FIG. 10, a cross-sectional view illustrating another such configuration shows multiple distal optical conduits 64A-I and the embedded cuff inflation conduit 58 embedded in the endotracheal tube wall 16.

Figure 11:
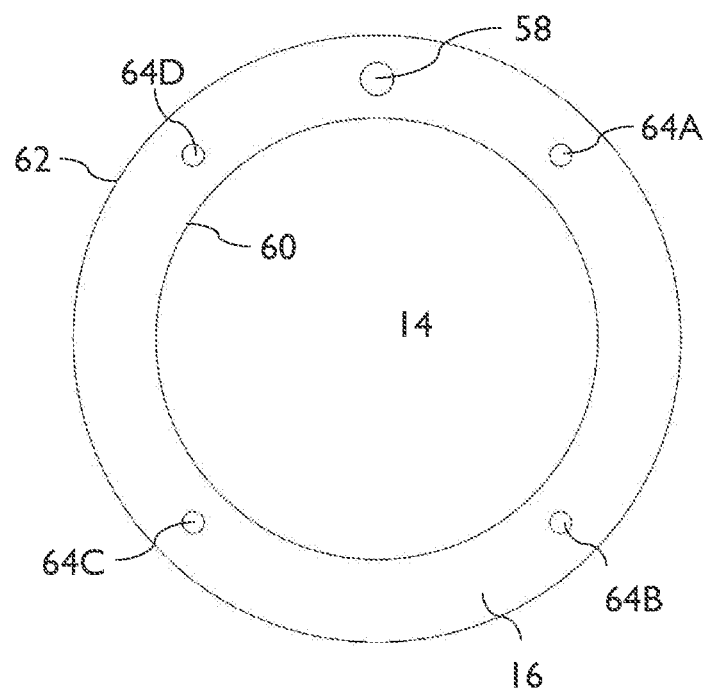
FIG. 11 is a cross sectional view of still another exemplary custom-made endotracheal tube showing an embedded cuff inflating conduit and smaller embedded optical conduits.

In the cross-sectional view of FIG. 11, another exemplary configuration is depicted as a variation of the orientations and size of the distal optical conduits 64A-D in the endotracheal tube wall 16.

Figure 12:
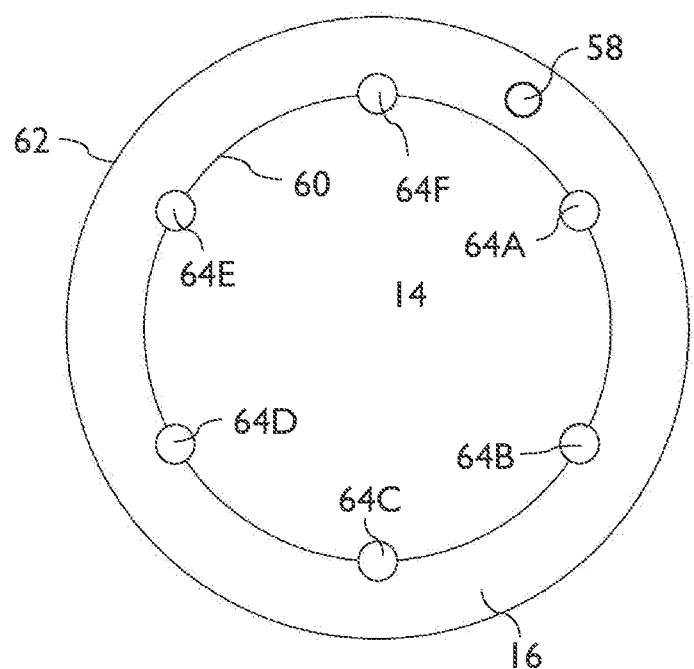
FIG. 12 is a cross sectional view of yet another exemplary custom-made endotracheal tube showing an embedded cuff inflating conduit and partially embedded optical conduits.

In FIG. 12, a cross-sectional view illustrates another exemplary configuration, wherein one or more distal optical conduits 64A-F may be located along the internal surface 60 of the endotracheal tube wall 16. As shown, they may be partially embedded within the endotracheal tube wall 16.

Figure 13:
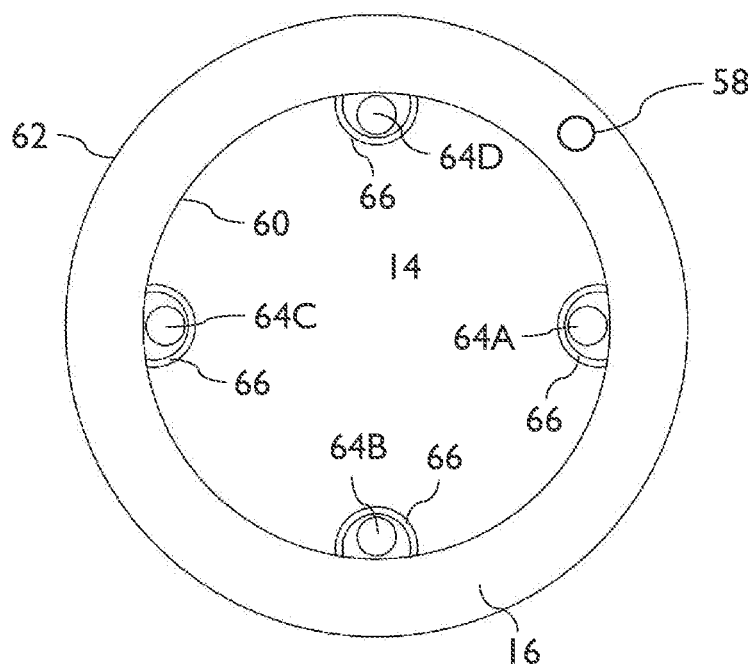
FIG. 13 is a cross sectional view of still another exemplary custom-made endotracheal tube showing an embedded cuff inflating conduit and secondary lumens for housing EMR conduction lines.

Referring now to FIG. 13, a cross-sectional view illustrates yet another exemplary configuration, wherein one or more distal optical conduits 64A-D may be located along the internal surface 60 of the endotracheal tube wall 56. Differing from FIG. 9, the distal optical conduits 64A-D are not embedded in the internal surface 60 of the endotracheal tube wall 16, but are associated with the internal surface 60, but may be enclosed within one or more optical conduit channels 66 that serve as secondary lumens to the main lumen 14.

In another exemplary embodiment, the EMR source 36 may also be incorporated into the ventilator itself, using the ventilator tubing as a conduit for passing the optical conduit 32 to the endotracheal tube body 20. The ventilator connection on the proximal end 22 of the endotracheal tube body 20 could then serve as a combined ventilator and optical conduit coupling apparatus. These connections could also be individual at the point of coupling with the endotracheal tube body 20.

In another embodiment, EMR is transmitted directly down the endotracheal tube wall 16 using the tube wall 16 as an optical conduit. This may be done in conjunction with any of the other EMR source 36 configurations specifically mentioned above or that would be understood by those skilled in the art armed with this disclosure.

Figure 14:
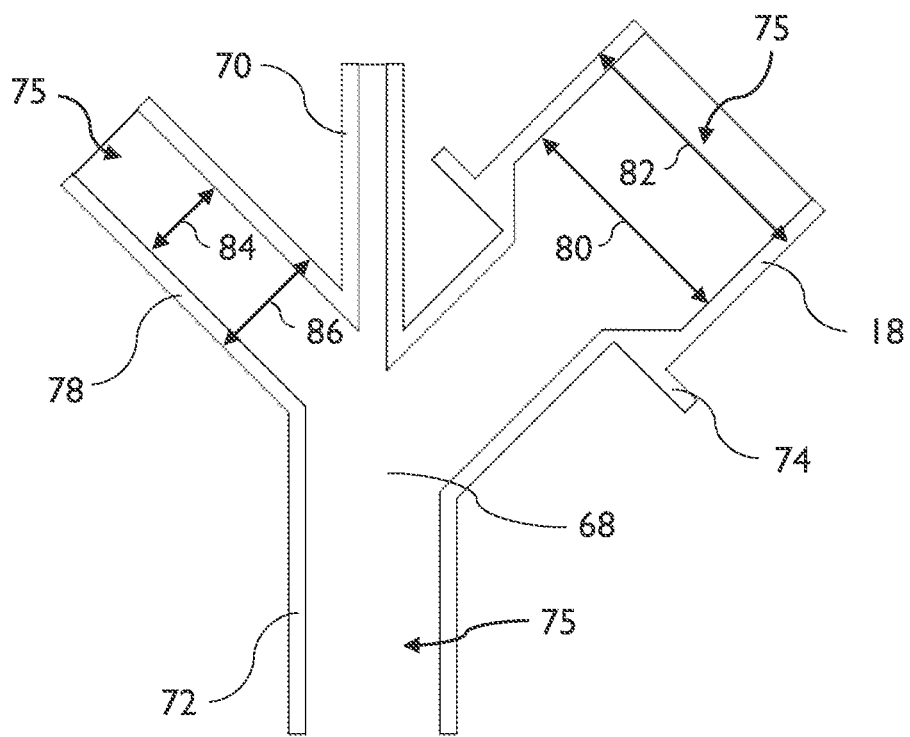
FIG. 14 is a profile, sectional view illustrating an exemplary embodiment of a tripartite port adapter for connection to an endotracheal tube, wherein the tripartite port adapter accommodates the connection of various-sized ventilator connectors in either male or female engagement and also accommodates the insertion of an EMR conduction line of an EMR delivery system into the endotracheal tube.

FIG. 14 is a profile, sectional view illustrating an exemplary embodiment of a port adapter 68 having a tripartite configuration for connection to an endotracheal tube 12, wherein the tripartite port adapter 68 accommodates the connection of various-sized ventilator connectors in either male or female engagement and also accommodates the insertion of an EMR conduction line 37 of an EMR delivery system 13 into the endotracheal tube 12. The tripartite port adapter 68 comprises ventilator collar 18, an EMR port 70, engagement end 72, and a secondary port 78. The ventilator collar 18, EMR port 70, engagement end 72, and secondary port 78 are angled from each other such that the multiple connections with ventilator, EMR delivery system 13, endotracheal tube 12, and any other type of device (a diagnostic probe, a therapeutic tool, an additional energy source, an optical device, a surgical instrument, a monitor, and the like) may be connected to the tripartite port adapter 68 without obstruction or interference.

The ventilator collar 18 has a first inner diameter 80 and a first outer diameter 82 that differs from the second inner diameter 84 and second outer diameter 86 of the secondary port 78 of the tripartite port adapter 68 so that the tripartite port adapter 68 can accommodate connection to ventilators having different-sized connectors. Of course, if any of the ventilator collar 18, EMR port 70, and secondary port 78 is not needed or is between uses, they may be capped so not to compromise ventilation of the patient.

As shown in FIG. 14, the tripartite port adapter 68 maybe retrofit between a ventilator and an endotracheal tube 12. However, it should be understood that a custom-made endotracheal tube 12 may be made by affixing the tripartite port adapter 68 (as the ventilator collar 18) directly to the tube body 20. To affix the tripartite adapter 68 directly to the tube body 20, any suitable coupling may be used, such as an adhesive, a pinch coupling, a male/female connection, or barbed inserted component, for example.

While specific embodiments and applications of the present disclosure have been illustrated and described, it is to be understood that the invention is not limited to the precise configuration and components disclosed as exemplary embodiments herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A therapeutic endotracheal tube assembly for connection to a ventilator for providing ventilation gas and for insertion into a patient's trachea to ventilate, to maintain patency of the patient's airway for delivery of the ventilation gas without obstruction or interference, and to deliver therapeutic electromagnetic radiation (EMR) to the patient, the therapeutic endotracheal tube assembly comprising:

an endotracheal tube having length, a longitudinal axis, a lumen defined by a tube wall, a ventilator collar with an engagement cylinder for connection to the ventilator, an upper tube portion having a proximate end coupled to the ventilator collar, and a lower tube portion having a forward end for insertion into the patient's trachea;
an EMR delivery system comprising:
an EMR source disposed external to the endotracheal tube for emitting non-ultraviolet, therapeutic EMR having an intensity comprising fluency of at least 0.2 kJ/cm$^2$ up to 1.0 kJ/cm$^2$, power of at least 0.005 mW to 1.0 W, and power density of 1.0 mW/cm$^2$ up to 1.0 W/cm$^2$, whereby such intensity is sufficient to activate desired therapeutic properties within the patient, the EMR source being configured to deliver sterilizing EMR and healing EMR in a treatment pattern selected from the group of treatment patterns consisting of emitting the sterilizing EMR and the healing EMR alternatively, alternatingly, and simultaneously;
an EMR conduction line conducive to the axial propagation of the non-ultraviolet, therapeutic EMR from the EMR source along the length of the endotracheal tube, the EMR conduction line having a coupling end, an emission portion, and a distal end and being removably insertable into the endotracheal tube to deliver non-ultraviolet, therapeutic EMR within the patient at sufficient intensity to activate desired therapeutic properties, the emission portion being distinct from the distal end and disposed within the lumen of the endotracheal tube upstream of the distal end such that EMR is emittable from the distal end and radially from the emission portion, the EMR conduction line being fully insertable into the lumen of the endotracheal tube such that the EMR conduction line inserted is encapsulated by the endotracheal tube and the distal end of the EMR conduction line is disposed proximate the forward end of the endotracheal tube; and
a coupling to connect the EMR source to the coupling end of the EMR conduction line; and
an endotracheal adapter removably connectable to and disposed intermediate of the ventilator collar and the ventilator, the endotracheal adapter comprising a ventilator fitting end, an adapter body having a body axis alignable with the longitudinal axis of the endotracheal tube, a ventilation channel, an engagement end, and an EMR port protruding from the adapter body at an acute angle from the body axis and providing a conduit through which the EMR conduction line may be inserted into and removed from the endotracheal tube, the ventilator fitting end having a configuration corresponding to the engagement cylinder of the ventilator collar and a central axis alignable with the longitudinal axis of the endotracheal tube so to be connectable to the ventilator, and the engagement end being configured to engage connectably the engagement cylinder of the ventilator collar and having a central axis alignable with the longitudinal axis of the endotracheal tube so to be connectable to the ventilator collar, wherein, without compromising ventilation operations by obstructing or interfering with the delivery of the ventilation gas, the EMR conduction line is removably insertable through the EMR port into the ventilation channel and into the lumen of the endotracheal tube such that the EMR conduction line is movable freely and axially relative to the endotracheal tube.

2. An assembly as in claim 1, wherein at least a portion of the endotracheal tube is at least one of optically clear and translucent so that the therapeutic EMR emits from the EMR conduction line at least one of internally and externally to the endotracheal tube.

3. An assembly as in claim 1, wherein the EMR source comprises an optical element, the optical element being selected from the group consisting of light emitting diodes, lasers, filtered fluorescents, filtered incandescents, and any combination thereof.

4. An assembly as in claim 1, wherein the EMR conduction line emits EMR from at least a portion of the EMR conduction line, emission of the EMR from the EMR conduction line being from the group of emissions consisting of radial, oblique, longitudinal, from the distal end, and any combination thereof.

5. An assembly as in claim 1, wherein the therapeutic EMR is delivered at a predetermined duty cycle.

6. An assembly as in claim 1, wherein the therapeutic EMR has at least one wavelength, each wavelength being within the range from 380 nm to 900 nm.

7. An assembly as in claim 6, wherein the at least one wavelength of therapeutic EMR comprises a predominant wavelength selected to sterilize one or more target organisms and selected from a group of wavelengths consisting of wavelengths centered about 400 nm, 405 nm, 415 nm, 430 nm, 440 nm, 455 nm, 470 nm, 475 nm, 660 nm, and 808 nm.

8. An assembly as in claim 7, wherein the predominant wavelength alternates between a first predominant wavelength and a second predominant wavelength in a selected treatment pattern.

9. An assembly as in claim 1, wherein the fluence of the therapeutic EMR is within a range from 0.5 kJ/cm$^2$ and 1.0 kJ/cm$^2$.

10. A therapeutic, retrofittable delivery assembly to deliver therapeutic electromagnetic radiation (EMR) into an existing endotracheal tube while intubated within a patient's trachea, the endotracheal tube having length, a longitudinal axis, a lumen defined by a tube wall, a ventilator collar with an engagement cylinder for connection to a ventilator, an upper tube portion having a proximate end coupled to the ventilator collar, and a lower tube portion having a forward end inserted into the patient's trachea for the delivery of ventilation gas, the therapeutic retrofittable delivery assembly comprising:
an EMR delivery system comprising:
an EMR source disposed external to the endotracheal tube for emitting non-ultraviolet, therapeutic EMR having an intensity comprising fluency of at least 0.2 kJ/cm$^2$ up to 1.0 kJ/cm$^2$, power of at least 0.005 mW to 1.0 W, and power density of 1.0 mW/cm$^2$ up to 1.0 W/cm$^2$, whereby such intensity is sufficient to activate desired therapeutic properties within the patient, the EMR source being configured to deliver sterilizing EMR and healing EMR in a treatment pattern selected from the group of treatment patterns consisting of emitting the sterilizing EMR and the healing EMR alternatively, alternatingly, and simultaneously;
a removably insertable EMR conduction line conducive to the axial propagation of EMR from the EMR source along the length of the EMR conduction line into the lumen of the endotracheal tube, the EMR conduction line having a coupling end, an emission portion, and a distal end, the emission portion being disposed within the endotracheal tube upstream of the distal end such that EMR is emittable from the distal end and radially from the emission portion, the EMR conduction line being fully insertable into the lumen of the endotracheal tube such that the EMR conduction line inserted is encapsulated by the endotracheal tube and the distal end of the EMR conduction line is disposed proximate the forward end of the endotracheal tube; and a coupling to connect the EMR source to the coupling end of the EMR conduction line; and an endotracheal adapter removably connectable to and disposed intermediate of the ventilator collar and the ventilator, the endotracheal adapter comprising a ventilator fitting end, an adapter body having a body axis alignable with the longitudinal axis of the endotracheal tube, a ventilation channel, an engagement end, and an EMR port protruding from the adapter body at an acute angle from the body axis and providing a conduit through which the EMR conduction line may be inserted into and removed from the endotracheal tube, and a secondary port, the ventilator fitting end having a configuration corresponding to the engagement cylinder of the ventilator collar and a central axis alignable with the longitudinal axis of the endotracheal tube so to be connectable to the ventilator, and the engagement end being configured to engage connectably the engagement cylinder of the ventilator collar and having a central axis alignable with the longitudinal axis of the endotracheal tube so to be connectable to the ventilator collar, wherein, without compromising ventilation operations by obstructing or interfering with the delivery of the ventilation gas, the EMR conduction line is removably insertable through the EMR port into the ventilation channel and into the lumen of the endotracheal tube such that the EMR conduction line is movable freely and axially relative to the endotracheal tube.

11. The retrofittable delivery assembly as in claim 10, wherein the removable EMR conduction line emits EMR from at least a portion of the EMR conduction line, emission of the EMR from the EMR conduction line being from the group of emissions consisting of radial, oblique, longitudinal, from the distal end, and any combination thereof.

12. The retrofittable delivery assembly as in claim 10, wherein the secondary port has an aperture through which at least one of a diagnostic probe, a therapeutic tool, an additional energy source, an optical device, a fluid retrieval device, a fluid delivery device, a surgical instrument, and a monitor passes into the lumen of the endotracheal tube.

13. The retrofittable delivery assembly as in claim 10, wherein the endotracheal adapter being removably connectable to the ventilator collar and ventilator such that the retrofittable delivery assembly is interchangeable between retrofitting to facilitate EMR delivery and the non-retrofitted intubation of the existing endotracheal tube.

14. An electromagnetic radiation (EMR) delivery system for removable insertion into an existing endotracheal tube while intubated within a patient's trachea to facilitate ventilating and maintaining patency of the patient's airway, the intubated endotracheal tube having length, a longitudinal axis, a lumen defined by a tube wall and a ventilator collar with an engagement cylinder for coupling the endotracheal tube to a ventilator for the delivery of ventilation gas, the EMR delivery system to deliver therapeutic EMR to the patient, the EMR delivery system comprising:

an EMR source disposed external to the endotracheal tube for emitting non-ultraviolet, therapeutic EMR having an intensity comprising fluency of at least 0.2 kJ/cm' up to 1.0 kJ/cm², power of at least 0.005 mW to 1.0 W, and power density of 1.0 mW/cm² up to 1.0 W/cm², whereby such intensity is sufficient to activate desired therapeutic properties within the patient, the EMR source being configured to deliver sterilizing EMR and healing EMR in a treatment pattern selected from the group of treatment patterns consisting of emitting the sterilizing EMR and the healing EMR alternatively, alternatingly, and simultaneously;

an EMR conduction line being removably insertable into the endotracheal tube while intubated and being conducive to the axial propagation of EMR from the EMR source along the length of the endotracheal tube, the EMR conduction line having a coupling end, an emission portion, and a distal end, the emission portion being disposed within the lumen of the endotracheal tube upstream of the distal end such that non-ultraviolet, therapeutic EMR is emittable from the distal end and radially from the emission portion, the EMR conduction line being fully insertable into the lumen of the endotracheal tube such that the EMR conduction line inserted is encapsulated by the endotracheal tube and the distal end of the EMR conduction line is disposed proximate the forward end of the endotracheal tube;

an endotracheal adapter removably connectable to and disposed intermediate of the ventilator collar and the ventilator, the endotracheal adapter comprising a ventilator fitting end, an adapter body having a body axis alignable with the longitudinal axis of the endotracheal tube, a ventilation channel, an engagement end, and an EMR port protruding from the adapter body at an acute angle from the body axis and providing a conduit through which the EMR conduction line may be inserted into and removed from the endotracheal tube, the ventilator fitting end having a configuration corresponding to the engagement cylinder of the ventilator collar and a central axis alignable with the longitudinal axis of the endotracheal tube so to be connectable to the ventilator, and the engagement end being configured to engage connectably the engagement cylinder of the ventilator collar and having a central axis alignable with the longitudinal axis of the endotracheal tube so to be connectable to the ventilator collar, wherein, without compromising ventilation operations by obstructing or interfering with the delivery of the ventilation gas, the EMR conduction line is removably insertable through the EMR port into the ventilation channel and into the lumen of the endotracheal tube such that the EMR conduction line is movable freely and axially relative to the endotracheal tube; and a coupling to connect the EMR source to a coupling end of the EMR conduction line.

15. The EMR delivery system as in claim 14, wherein the endotracheal adapter further comprises a secondary port having an aperture through which at least one of a diagnostic probe, a therapeutic tool, an additional energy source, an optical device, a fluid retrieval device, a fluid delivery device, a surgical instrument, and a monitor passes into the lumen of the endotracheal tube.

16. The EMR delivery system as in claim 14, wherein the endotracheal adapter being removably connectable to the ventilator collar such that the EMR delivery system 3 interchangeable between retrofitting to facilitate EMR delivery and a non-retrofitted intubation of the existing endotracheal tube.

* * * * *